US010751133B2

(12) United States Patent
Toporek et al.

(10) Patent No.: US 10,751,133 B2
(45) Date of Patent: Aug. 25, 2020

(54) MARKERLESS ROBOT TRACKING SYSTEMS, CONTROLLERS AND METHODS (71) Applicant: KONINKLIJKE PHILIPS N.V., Eindhoven (NL)

(72) Inventors: Grzegorz Andrzej Toporek, Boston, MA (US); Aleksandra Popovic, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/498,000

(22) PCT Filed: Mar. 28, 2018

(86) PCT No.: PCT/EP2018/057919
§ 371 (c)(1),
(2) Date: Sep. 26, 2019

(87) PCT Pub. No.: WO2018/178150
PCT Pub. Date: Oct. 4, 2018

(65) Prior Publication Data
US 2020/0038116 A1 Feb. 6, 2020

Related U.S. Application Data (60) Provisional application No. 62/479,852, filed on Mar. 31, 2017.

(51) Int. Cl.
H04N 5/225 (2006.01)
A61B 34/20 (2016.01)
(Continued)

(52) U.S. Cl.
CPC .............. A61B 34/20 (2016.02); A61B 34/30 (2016.02); G06T 7/73 (2017.01);
(Continued)

(58) Field of Classification Search
CPC . A61B 34/20; A61B 34/30; A61B 2034/2065; A61B 2034/2059;
(Continued)

(56) References Cited

U.S. PATENT DOCUMENTS 8,108,072 B2  1/2012 Zhao
8,668,345 B2  3/2014 Shafer
(Continued)

FOREIGN PATENT DOCUMENTS

WO   2009045827   4/2009
WO   2012158458   11/2012
WO   2016/141378   9/2016

OTHER PUBLICATIONS

International Search Report and Written Opinion dated Jun. 12, 2018 for International Application No. PCT/EP2018/057919 Filed Mar. 28, 2018.
(Continued)

Primary Examiner — Robert Chevalier (57) ABSTRACT

A markerless robot tracking system (10) employing a surgical RCM robot (20) including a primary revolute joint (22) rotatable about a primary rotational axis and a secondary revolute joint (22) rotatable about a secondary rotational axis. A plurality of unique landmark sets are integrated into the robot (20) with each unique landmark set including landmark(s) (30) in a fixed orientation relative to the primary rotational axis and further including additional landmark(s) (30) in a fixed orientation relative to the secondary rotational axis. The system (10) further an optical camera (41, 51) for visualizing a subset of the plurality of unique landmark sets within a camera coordinate system (43, 53), and a robot tracking controller (70) for estimating a robot pose of the surgical RCM robot (20) within the camera coordinate system (43, 53) derived from the visualization by
(Continued)

the optical camera (41, 51) of the subset of landmark(s) within the camera coordinate system (43, 53).

20 Claims, 4 Drawing Sheets

(51) Int. Cl.
*A61B 34/30* (2016.01)
*G06T 7/73* (2017.01)
*H04N 7/18* (2006.01)

(52) U.S. Cl.
CPC ............... *A61B 2034/2051* (2016.02); *A61B 2034/2057* (2016.02); *A61B 2034/2059* (2016.02); *A61B 2034/2065* (2016.02); *G06T 2207/30244* (2013.01)

(58) Field of Classification Search
CPC .... A61B 2034/2051; A61B 2034/2057; G06T 7/73; G06T 2207/30244
USPC ............... 348/169, 135, 137, 143, 152, 136
See application file for complete search history.

(56) References Cited

U.S. PATENT DOCUMENTS

| | | | |
|---|---|---|---|
| 2002/0082498 A1* | 6/2002 | Wendt | ............... H04N 13/246 600/411 |
| 2005/0004449 A1 | 1/2005 | Mitschke | |
| 2006/0142657 A1 | 6/2006 | Quaid | |
| 2007/0265527 A1 | 11/2007 | Wohlgemuth | |
| 2009/0041565 A1 | 2/2009 | Rodriguez | |
| 2010/0168763 A1 | 7/2010 | Zhao | |
| 2010/0256960 A1 | 10/2010 | Ortmaier | |

OTHER PUBLICATIONS

Chung, et al: "An Image-Guided Robotic Surgery System for Spinal Fusion", International Journal of Control, Automation, and Systems, vol. 4, No. 1, pp. 30-41, Feb. 2006.

Kostrzewski, et al: "Robotic system for cervical spine surgery", Int J Med Robotics Comput Assist Surg (2011).

Tian, et al: "A Robot-Assisted Surgical System Using a Force-Image Control Method for Pedicle Screw Insertion", PLOS ONE, Jan. 2014 | vol. 9 | Issue |.

Cornella, et al: "Improving Cartesian Position Accuracy of a Telesurgical Robot", 2008 IEEE.

Reiter, et al: "Marker-less Articulated Surgical Tool Detection", Proc. Comput. Assist. Radiol. Surg. vol. 7, 2012.

\* cited by examiner

MARKERLESS ROBOT TRACKING SYSTEMS, CONTROLLERS AND METHODS

CROSS REFERENCE TO RELATED APPLICATIONS

This application is the U.S. National Phase application under 35 U.S.C. § 371 of International Application No. PCT/EP2018/057919 filed Mar. 28, 2018, published as WO 2018/178150 on Oct. 4, 2018, which claims the benefit of U.S. Provisional patent Application No. 62/479,852 filed Mar. 31, 2017. These applications are hereby incorporated by reference herein.

FIELD OF THE INVENTION

The inventions of the present disclosure generally relate to systems, controllers and methods utilizing trackable markers attached to a surgical robot for purposes of tracking a pose of the surgical robot within a camera coordinate system (e.g., a tracking of optical markers in a coordinate system of an optical position measurement system or a tracking of electromagnetic sensors in a coordinate system of an electromagnetic position measurement system).

The inventions of the present disclosure more particularly relate to improving such systems, controllers and methods by integrating trackable landmarks into the surgical robot for purposes of estimating a pose of the surgical robot within a coordinate system of a position measurement system (e.g., an optical position measurement system or a monocular position measurement system).

BACKGROUND OF THE INVENTION

In most of the image-guided procedures, after registration, tracked surgical instruments are co-displayed with the previously acquired medical images. Such display visualization of an instrument position in respect to a patient coordinate system has shown to be beneficial for various clinical procedures, particularly procedures involving intra-operative confirmation of the position of the surgical instrument in relation to critical anatomical structures.

Tracking of the surgical instruments (e.g., tissue resection devices, ultrasound transducers, needles, etc.) may be enabled by external position measurement systems (e.g., an optical position measurement system, electromagnetic position measurement system, etc.). In case of robotic surgical tools, tracking with electromagnetic sensors has proven to be impracticable in view of an accuracy of electromagnetic tracking is susceptible to ferromagnetic materials, which are not only present in the operating room but are also commonly used in surgical robotic systems (e.g., stainless steel instruments and robotic arms, electrical motors, etc.).

On the other hand, both high accuracy and ease of integration of optical tracking has made optical tracking technology very popular among the technical community. The most common method is to use external markers that are attached to the arm of the robot. For example, retro-reflective markers in conjunction with an infrared optical tracking system have been used to detect the motion of the robotic arm and reduce Cartesian position error of the robot. Optical tracking using retroreflective markers has also been investigated for minimally invasive robot-assisted pedicle screw placement as well as spinal fusion, where optical marker are mounted on both the robot end-effector and patient's vertebras and used later on for navigation. Another patient-to-robot registration method has been incorporated into a robotic system described where the method involves a coarse registration using point-based matching, and a fine alignment based on the surface matching.

SUMMARY OF THE INVENTION

To improve upon marker based tracking systems, controllers and methods for tracking a pose of a surgical RCM robot within a camera coordinate system, the present disclosure provides inventions for estimating a pose of a surgical RCM robot within a coordinate system of a position measurement system based on a visualization within the camera coordinate system of unique landmarks sets integrated into the surgical RCM robot.

One embodiment of the inventions of the present disclosure a markerless robot tracking system comprising a surgical RCM robot transitionable between a plurality of poses within a robot coordinate system.

The surgical RCM robot includes a primary revolute joint rotatable about a primary rotational axis and a secondary revolute joint rotatable about a secondary rotational axis.

A plurality of unique landmark sets are integrated into the surgical RCM robot. Each unique landmark set includes one or more landmarks at a fixed orientation relative to the primary rotational axis, and further includes an additional one or more landmarks at a fixed orientation relative to the secondary rotational axis.

The system further employs an optical camera and a robot tracking controller for tracking the surgical RCM robot.

In operation, the optical camera visualizes of a subset of landmarks or all of the landmarks within a camera coordinate system. The subset of the landmark includes two or more landmarks from one or more of the unique landmark sets.

The robot tracking controller controls an estimation of a robot pose of the surgical RCM robot within the camera coordinate system in response to receiving a visualization by the optical camera of the subset of landmarks within the camera coordinate system.

The estimation of the robot pose of the surgical RMC robot within the camera coordinate system may involve an estimation by the robot tracking controller of a translation alignment and/or a rotation orientation between the robot coordinate system and the camera coordinate system.

A second embodiment of the inventions of the present disclosure is a markerless robot tracking device comprising the robot pose controller for controlling the estimation of the robot pose of the surgical RCM robot within the camera coordinate in response to receiving the visualization by the optical camera of the subset of landmarks within the camera coordinate system, and for further generating surgical RCM robot pose data informative of the estimation of the robot pose of the surgical RCM robot within the camera coordinate system.

The surgical RCM robot pose data may be processed for any purpose of an interventional procedure including, but not limited to, a transformation of the robot pose of the surgical RCM robot within the camera coordinate system into an image coordinate system associated within an interventional image of a patient (e.g., a CT image, a MRI image, an X-ray image, an ultrasound image, etc.) whereby a robot instrument (e.g., a needle, a pedicle screw, etc.) may be overlayed within the interventional image of the patient and/or whereby an image generated by a robot instrument (e.g., an endoscope, etc.) may be fused with the interventional image of the patient.

A third embodiment of the inventions of the present disclosure a markerless robot tracking method for tracking the surgical RCM robot.

The markerless robot tracking method comprises the surgical RCM robot being selectively transitioned between a plurality of robot poses within a robot coordinate system, an optical camera visualizing a subset of landmarks or all of the landmarks within a camera coordinate system, and a robot tracking controller controlling an estimation of a robot pose of the surgical RCM robot within the camera coordinate system derived from the visualizing by the optical camera of subset of landmarks or all of the landmarks within the camera coordinate system.

For purposes of describing and claiming the inventions of the present disclosure:

(1) terms of the art of the present disclosure including, but not limited to, "landmark", "coordinate system", "pose", "arms" "arcs", "revolute joints", "stereoscopic camera", "monocular camera", "translation vector" and "rotation orientation" are to be understood as known in the art of the present disclosure and exemplary described in the present disclosure;

(2) the term "surgical RCM robot", broadly encompasses all surgical robots, as known in the art of the present disclosure and hereinafter conceived, structurally arranged with two or more revolute joints having rotational axis that intersect at a remote center of motion (RCM);

(3) the term "unique landmark set" broadly encompasses a set of landmarks having a common descriptor that is distinct from descriptor of other set(s) of landmarks as exemplary described in the present disclosure. Examples of a descriptor include, but are not limited to, dimensions and geometrical configurations for the landmarks;

(4) the term "position measurement system" broadly encompasses all systems, as known in the art of the present disclosure and hereinafter conceived, including an optical camera to visualize features of a surgical RCM robot. Examples of a position measurement system include, but are not limited to, an optical position measurement system (e.g., the NDI Polaris Spectra) and a monocular position measurement system (e.g., the MicronTracker, and the ClaroNav). Examples of an optical camera include, but are not limited to, a stereoscopic camera and a monocular camera;

(5) the term "markerless robot tracking system" broadly encompasses all robot tracking systems, as known in the art of the present disclosure and hereinafter conceived, incorporating the inventive principles of the present disclosure for estimating a pose of a surgical RCM robot within a coordinate system of a position measurement system based a visualization within the camera coordinate system of unique landmarks sets integrated into the surgical RCM robot as exemplary described in the present disclosure. Examples of known robot tracking systems include, but are not limited to, camera-based systems with depth sensors (e.g. Microsoft Kinect), time-of-flight sensors (e.g. Swissranger SR 4000).

(6) the term "markerless robot tracking method" broadly encompasses all robot tracking methods, as known in the art of the present disclosure and hereinafter conceived, incorporating the inventive principles of the present disclosure for estimating a pose of a surgical RCM robot within a coordinate system of a position measurement system based a visualization within the camera coordinate system of unique landmarks sets integrated into the surgical RCM robot as exemplary described in the present disclosure. Examples of known robot tracking methods include, but are not limited to, all types of camera based tracking methods using single camera and multiple-view reconstruction, time-of-flight cameras, cameras with depth sensors (e.g. Microsoft Kinect), and scene learning methods (e.g. using convolutional neural networks).

(7) the term "controller" broadly encompasses all structural configurations of an application specific main board or an application specific integrated circuit for controlling an application of various inventive principles of the present disclosure related to estimating a pose of a surgical RCM robot within a coordinate system of a position measurement system based a visualization within the camera coordinate system of unique landmarks sets integrated into the surgical RCM robot as exemplary described in the present disclosure. The structural configuration of the controller may include, but is not limited to, processor(s), computer-usable/computer readable storage medium(s), an operating system, application module(s), peripheral device controller(s), interface(s), bus(es), slot(s) and port(s). The labels "robot actuation" and "robot tracking" as used herein for the term "controller" distinguishes for identification purposes a particular controller from other controllers as described and claimed herein without specifying or implying any additional limitation to the term "controller";

(8) the term "application module" broadly encompasses a component of an controller consisting of an electronic circuit and/or an executable program (e.g., executable software and/or firmware stored on non-transitory computer readable medium(s)) for executing a specific application. The labels "translation vector estimator", "rotational orientation estimator" and "robot pose estimator" as used herein for the term "application module" distinguishes for identification purposes a particular application module from other application module as described and claimed herein without specifying or implying any additional limitation to the term "application module"; and (9) the terms "data", and "command" broadly encompasses all forms of a detectable physical quantity or impulse (e.g., voltage, current, or magnetic field strength) as understood in the art of the present disclosure and as exemplary described in the present disclosure for communicating information and/or instructions in support of applying various inventive principles of the present disclosure as subsequently described in the present disclosure. Data/command communication between components of the present disclosure may involve any communication method, as known in the art of the present disclosure and hereinafter conceived, including, but not limited to, data/command transmission/reception over any type of wired or wireless medium/datalink and a reading of data/command uploaded to a computer-usable/computer readable storage medium.

The foregoing embodiments and other embodiments of the inventions of the present disclosure as well as various features and advantages of the inventions of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of the present disclosure being defined by the appended claims and equivalents thereof.

DETAILED DESCRIPTION OF THE PREFERRED EMBODIMENTS

As an improvement of marker based tracking systems, controllers and methods for tracking a pose of a surgical robot within a camera coordinate system, the present disclosure provides inventions for estimating a pose of a surgical RCM robot within a camera coordinate system based a visualization within the camera coordinate system of unique landmarks sets integrated into the surgical RCM robot.

Figure 1:
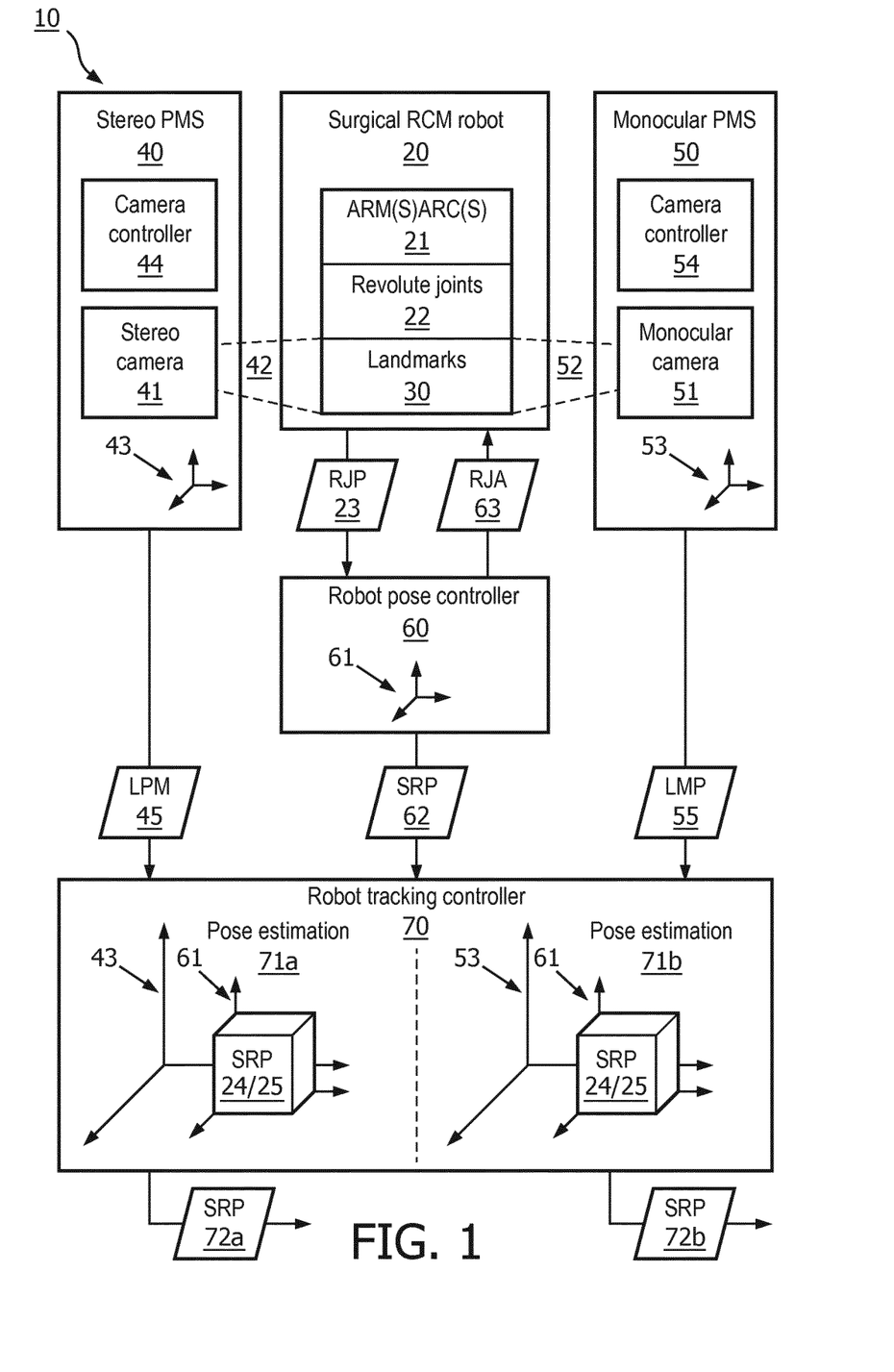
FIG. 1 illustrates an exemplary embodiment of a markerless robot tracking system in accordance with the inventive principle of the present disclosure.
Figure 2A:
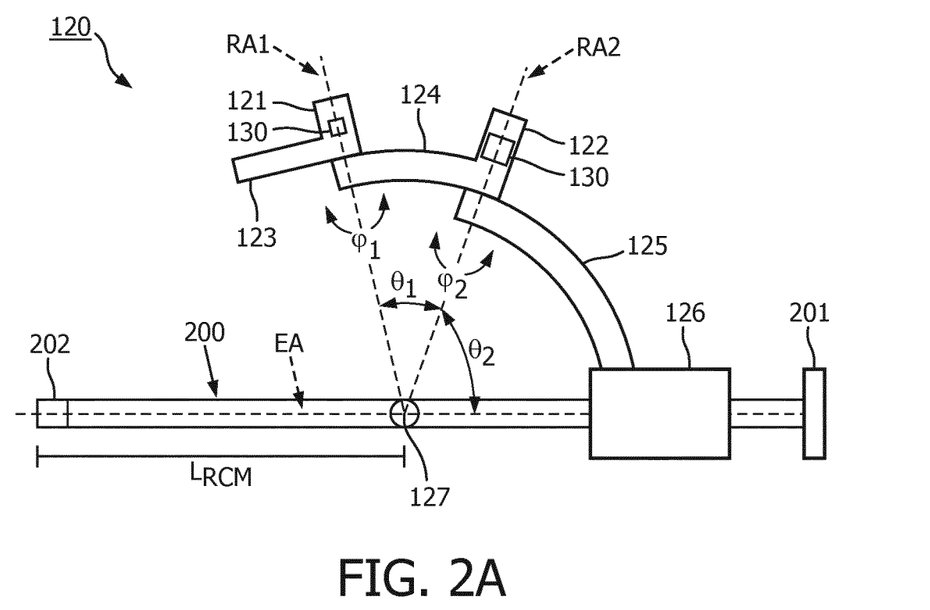
FIGS. 2A-2C illustrates an exemplary embodiment of a surgical RCM robot in accordance with the inventive principle of the present disclosure.
Figure 2B:
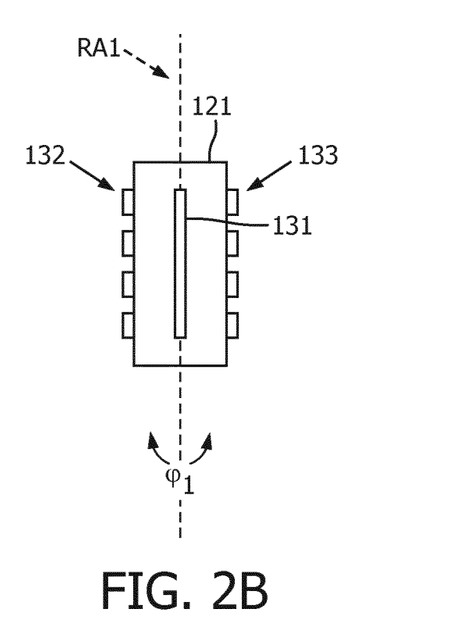
Figure 2C:
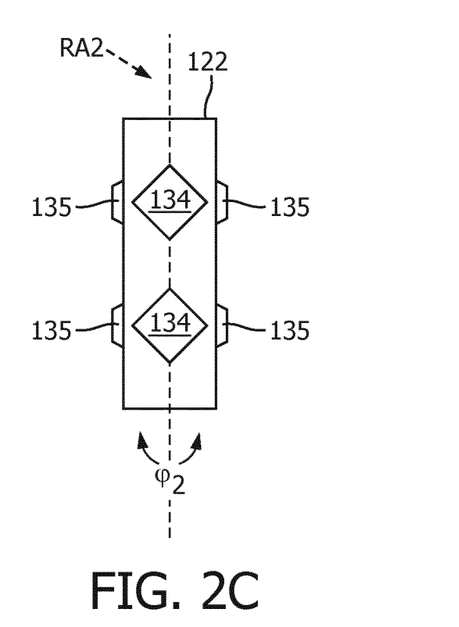

To facilitate an understanding of the various inventions of the present disclosure, the following description of FIGS. 1-2C teaches embodiments of a markerless robot tracking system 10 and a landmarked surgical RCM robot 20 in accordance with the inventive principles of the present disclosure. From this description, those having ordinary skill in the art will appreciate how to practice various and numerous embodiments of markerless tracking systems and landmarked surgical RCM robots in accordance with the inventive principles of the present disclosure.

Also from this description, those having ordinary skill in the art will appreciate an incorporation of a markerless tracking system of the present disclosure in numerous and various types of image-guided interventions utilizing a landmarked surgical RCM robot of the present disclosure. Examples of such image-guided intervention include, but is not limited to, minimally invasive laparoscopic surgeries (e.g., prostatectomy, splenectomy, nephrectomy, hepatectomy, lobectomy, etc.) and minimally invasive surgeries of the spine (e.g., pedicle screw placement, decompression, spinal fusion, etc.).

Referring to FIG. 1, a markerless robot tracking system 10 of the present disclosure employs a surgical RCM robot 20.

Surgical RCM robot 20 has a structural arrangement of two (2) or more arms/arcs 21, and one (1) or more revolute joints 22 for defining a remote center of motion (RCM) established by an intersection of rotational axes of revolute joints 22 as known in the art of the present disclosure.

In accordance with the inventive principles of the present disclosure, two (2) or more unique sets of landmarks 30 are integrated into arms/arcs 21 and/or preferably revolute joints 22 as shown for purposes of estimating a pose of surgical RCM robot 20 within a camera coordinate system as will be further described in the present disclosure.

In practice, each unique landmark set include identical landmarks having common descriptors (e.g., same dimensions and same geometrical configurations), and the common descriptors among the unique landmark sets are dissimilar to a degree that facilitates a visual distinction between the unique landmark sets as will be further described in the present disclosure.

Further in practice, an integration of each unique set of landmarks 30 into arms/arcs 21 and/or preferably revolute joints 22 defines a unique location of a fixed orientation of each landmark 30 of a particular unique set relative to a rotational axis(es) of revolute joint(s) 22 for purposes of a differential visualization of each landmark 30 of a particular unique set by an optical camera as will be further described in the present disclosure.

Also in practice, a structural configuration and material composition of landmarks 30 are dependent upon the structural configuration of a particular embodiment of surgical RCM robot 20 and a particular type of position measurement system employed by markerless robot tracking system 10.

In a first embodiment, a landmark 30 is an external retro-reflective object that is detectable with a line-of-sight of an optical camera as known in the art of the present disclosure (e.g., a stereoscopic camera). Examples of such retro-reflective objects include, but are not limited to, prisms materially composed of a retro-reflective foil as known in the art of the present disclosure (e.g., spheres materially composed of a retro-reflective foil).

In a second embodiment, a landmark 30 is an external geometrical structure of an arc 21 or a revolute joint 22 that is detectable within camera images of a camera using a computer vision algorithm as known in the art of the present disclosure (e.g., a monocular camera). Examples of such external features include, but not limited to, a line (e.g., non-dashed or dashed, straight or curved) and a closed shape (e.g., a circle, an ellipse, a hexagon, etc.).

FIG. 2A illustrates an exemplary surgical RCM robot 120 employing a primary revolute joint 121 rotatable about a rotation axis RA1, a secondary revolute joint 122 rotatable about a rotation axis RA2, an arm 123, a support arc 124, and an instrument arc 125 including an end-effector 126 serving a guide for holding a metallic endoscope 200 having a rotation axis EA as shown or any other robot instrument (e.g., a needle, a pedicle screw, etc.). Support arc 124 is concentrically connected to revolute joint 121 and revolute joint 122, and instrument arc 125 is concentrically connected to revolute joint 122. More particularly, 1. rotational axes RA1, RAD and EA intersect at a remote center of motion 127 of surgical RCM robot 120,
2. a base arc length of $\theta_B$ of support arc 124 extends between rotation axes RA1 and RA2,
3. an extension arc length $\theta_{E1}$ of instrument arc 125 extends between rotation axes RA1 and EA,
4. a motorized actuator of primary revolute joint 121 may be operated to co-rotate arcs 124 and 125 about rotation axis RA1 for a desired $\varphi_1$ degrees to control a broad movement of distal focal tip 202 of endoscope 200 within workspace 37a,
5. a motorized actuator of secondary revolute joint 122 may be operated to rotate instrument arc 125 about rotation axis RA2 for a desired $\varphi_2$ degrees to control a targeted movement of distal focal tip 202 of endoscope 200,
6. end effector 126 has a capability, manual or controlled, of rotating endoscope 200 about its rotation axis EA,
7. an RCM length $L_{RCM}$ is a distance between RCM 127 and distal focal tip 202, and
8. an focal length (not shown) is a length of a field-of-view of the endoscope 200 extending from distal focal tip 202 as viewable from an eyepiece 201 of endoscope 200.

In practice, those having ordinary skill in the art of the present disclosure will appreciate other instruments that may be guided by surgical RCM robot 120.

In accordance with the inventive principles of the present disclosure, unique sets of landmarks 130 as symbolically shown are integrated into revolute joint 121 and revolute joint 122 at a fixed orientation relative to the rotational axes for purposes of estimating a pose of surgical RCM robot 120 within a camera coordinate system as will be further described in the present disclosure. Concurrently or alternatively, landmarks may be integrated into arcs 124 and 125 at a fixed orientation relative to the rotational axes.

For example, as shown in FIG. 2B, a unique set of a non-dashed line landmark 131 and a 180° opposing another non-dashed line landmark (not shown), and a unique set of dashed line landmarks 132 and 133 are equally spatially arranged in a fixed orientation around a rotation axis RA1 of revolute joint 121. These landmarks may or may not be materially composed of retro-reflective foil. For this example, the same unique sets of landmarks may also be integrated into revolute joint 122 and/or different unique sets of landmarks may be integrated into revolute joint 122.

By further example, as shown in FIG. 2C, a unique set of diamond landmarks 134 and a 180° opposing pair of diamond landmarks (not shown), and a unique set of a pair of trapezoid landmarks 135 are equally spatially arranged in a fixed orientation around a rotation axis RA2 of revolute joint 122. These landmarks may or may not be materially composed of retro-reflective foil. For this example, the same unique sets of landmarks may also be integrated into revolute joint 121 and/or different unique sets of landmarks may be integrated into revolute joint 121.

FIGS. 2B and 2C are non-limiting examples of the numerous and varied embodiments of an integration of unique sets of landmarks in a surgical RCM robot.

In practice, markerless robot tracking system 10 may further employ an actuatable platform (not shown for clarity) including link(s) and joint(s) for rotating and/or translating surgical RCM robot 120 within a global coordinate system as known in the art of the present disclosure.

Referring back to FIG. 1, markerless robot tracking system 10 of the present disclosure further employs one (1) or more optical position measurement systems including a stereoscopic position measurement system 40 and a monocular position measurement system 50.

Stereoscopic position measurement system 40 includes a stereoscopic camera 41 having a line-of-sight 42 for visualizing landmark(s) 30 within a camera coordinate system 43 calibrated to line-of-sight 42 as known in the art of the present disclosure. In practice, at any instantaneous moment, one or more landmark(s) 30 will be visible within line-of-sight 42 of stereoscopic camera 41 as surgical RCM robot 20 is transitioned between a plurality of poses relative to stereoscopic camera 41 as will be further described in the present disclosure.

Stereoscopic position measurement system 40 further includes a stereoscopic camera controller 44 for controlling an operation of stereoscopic camera 41 whereby controller 44 generates landmark position data 45 informative of an estimation of a three-dimensional ("3D") position (i.e., location and orientation) within camera coordinate system 43 of each landmark 30 visualized by stereoscopic camera 41 on a temporal basis as known in the art of the present disclosure.

Monocular position measurement system 50 includes a monocular camera 51 having a line-of-sight 52 for visualizing landmark(s) 30 within a camera coordinate system 53 calibrated to line-of-sight 52 as known in the art of the present disclosure. In practice, at any instantaneous moment, one or more landmark(s) 30 will be visible within line-of-sight 52 of monocular camera 51 as surgical RCM robot 20 is transitioned between a plurality of poses relative to monocular camera 51 as will be further described in the present disclosure.

Monocular position measurement system 50 further includes a monocular camera controller 54 for controlling an operation of monocular camera 51 whereby controller 54 generates landmark position data 55 informative of an estimation of a three-dimensional ("3D") position (i.e., location and orientation) within camera coordinate system 53 of each landmark 30 visualized by monocular camera 51 on a temporal basis as known in the art of the present disclosure.

Still referring to FIG. 1, markerless robot tracking system 10 of the present disclosure further employs a robot pose controller 60 and a robot tracking controller 70.

Robot pose controller 60 is structurally configured as known in the art of the present disclosure to communicate revolute joint actuation commands 63 to one or more revolute joint(s) 22 to thereby rotate a revolute joint 22 relative to its rotation axis to a degree specified by an image-guided intervention. Robot pose controller 60 may employ modules (not shown) for implementing the image-guided intervention or may receive commands from an image-guided controller (not shown) as known in the art of the present disclosure.

Robot pose controller 60 is further structurally configured as known in the art of the present disclosure to receive revolute joint position data 23 informative of a rotational position of each revolute joint 22 relative to its rotation axis via an encoder or other position sensors are known in the art of the present disclosure. Robot pose controller 60 processes revolute joint position data 23 relative to a robot coordinate system 61 to generate surgical robot pose data 62 informative a pose of surgical RCM robot 20 within robot coordinate system 120.

Robot tracking controller 70 is structurally configured in accordance with the inventive principles of the present disclosure to estimate a pose 25 of surgical RCM robot 20 within a camera coordinate system (e.g., camera coordinate system 43 of stereoscopic position measurement system 40 or camera coordinate system 53 of monocular position measurement system 50).

In practice, robot tracking controller 70 interprets landmark position data (e.g., landmark position data 45 of stereoscopic position measurement system 40 or landmark position data 55 of monocular position measurement system 50) and surgical robot pose data 62 to estimate pose 25 of surgical RCM robot 20 within the camera coordinate system.

In practice, robot tracking controller 70 may implement any technique as known in the art of the present robot whereby robot tracking controller 70 interprets the landmark position data and surgical robot pose data 62 to ascertain a transformation alignment between the camera coordinate system and robot coordinate system 61 to thereby transform a pose 24 of surgical RCM robot 20 within robot coordinate system 61 to estimated pose 25 of surgical RCM robot 20 within the camera coordinate system.

In one embodiment, robot tracking controller 70 interprets the landmark position data and surgical robot pose data 62 to yields a translation vector and/or a rotation matrix as variables for transforming a pose 24 of surgical RCM robot 20 within robot coordinate system 61 to estimated pose 25 of surgical RCM robot 20 within the camera coordinate system.

The translation vector defines a translation alignment between the origins of robot coordinate system 62 and the camera coordinate system as will be further described in the present disclosure.

The rotation matrix defines a rotational orientation of the axes of robot coordinate system 62 and the camera coordinate system as will be further described in the present disclosure.

In one stereoscopic embodiment, robot tracking controller 70 implements a pose determination 71 involving an interpretation of landmark position data 45 and surgical robot pose data 62 yielding a translation vector and a rotation matrix as variables for transforming pose 24 of surgical RCM robot 20 within robot coordinate system 61 to estimated pose 25 of surgical RCM robot 20 within camera coordinate system 43. Robot tracking controller 70 generates estimated surgical robot pose data 72a being informative of estimated pose 25 of surgical RCM robot 20 within camera coordinate system 43, and communicates estimated surgical robot pose data 72 to robot pose controller 60 or any other controller (not shown) for utilizing estimated surgical robot pose data 72 to control a selective actuation of surgical RCM robot 20 by robot pose controller 60 in accordance with an image-guided intervention or any other applicable intervention.

In a monocular embodiment, robot tracking controller 70 implements a pose determination 72 involving an interpretation of landmark position data 45 and surgical robot pose data 62 yielding a translation vector and a rotation matrix as variables for transforming pose 24 of surgical RCM robot 20 within robot coordinate system 61 to estimated pose 25 of surgical RCM robot 20 within camera coordinate system 53. Robot tracking controller 70 generates estimated surgical robot pose data 72b being informative of estimated pose 25 of surgical RCM robot 20 within camera coordinate system 53, and communicates estimated surgical robot pose data 72 to robot pose controller 60 or any other controller (not shown) for utilizing estimated surgical robot pose data 72 to control a selective actuation of surgical RCM robot 20 by robot pose controller 60 in accordance with an image-guided intervention or any other applicable intervention.

To facilitate a further understanding of the various inventions of the present disclosure, the following description of FIGS. 3-6 teaches embodiments of a markerless robot tracking system 110 employing landmarked surgical robot 120 (FIG. 2A) in accordance with the inventive principles of the present disclosure. From this description, those having ordinary skill in the art will further appreciate how to practice various and numerous embodiments of markerless tracking systems and landmarked surgical RCM robots in accordance with the inventive principles of the present disclosure.

Figure 3:
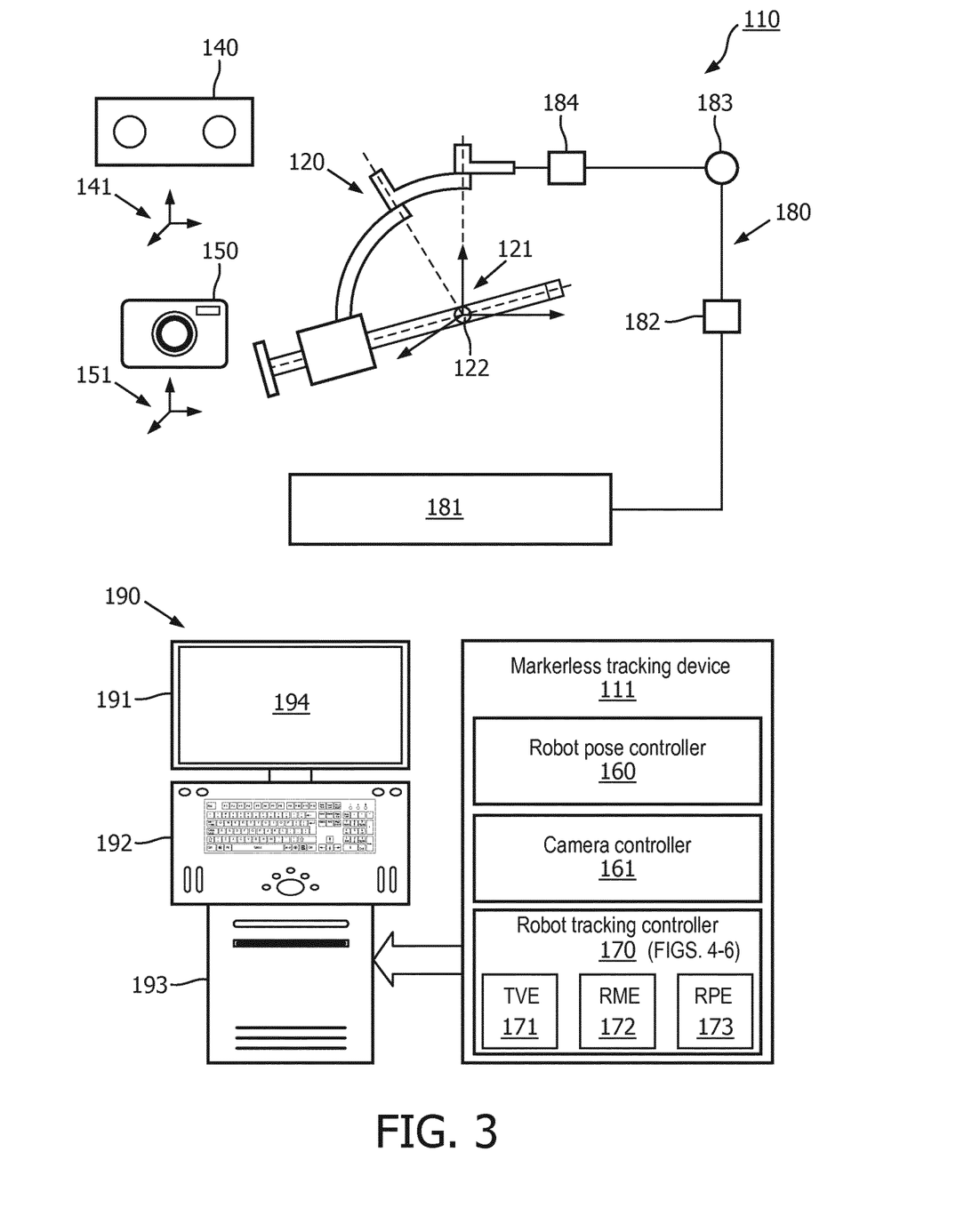
FIG. 3 illustrates an exemplary embodiment of the markerless robot tracking system shown in FIG. 1 in accordance with the inventive principle of the present disclosure.

Referring to FIG. 3, markerless robot tracking system 110 employs an active arm 180 attached to a table 181 whereby surgical RCM robot 120 (FIG. 2A) may be rotated and/or translated relative to table 181 within a global coordinate system (not shown). To this end, active arm 180 includes a translation joint 182, a rotational joint 183 and a translation joint 184 as known in the art of the present disclosure.

Markerless robot tracking system 110 further employs a stereoscopic camera 140 having a line-of-sight (not shown) calibrated to a camera coordinate system 141 and/or a monocular camera 150 having a line-of-sight (not shown) calibrated to a camera coordinate system 151.

Markerless robot tracking system 110 further employs a workstation 190, and a markerless robot tracking device 111 including a robot pose controller 160, a camera controller 161 and a robot tracking controller 170.

Workstation 190 including a known arrangement of a monitor 191, a keyboard 192 and a computer 193 as known in the art of the present disclosure.

Robot pose controller 160, camera controller 161 and robot tracking controller 170 are installed in computer 193, and each controller may include a processor, a memory, a user interface, a network interface, and a storage interconnected via one or more system buses.

The processor may be any hardware device, as known in the art of the present disclosure or hereinafter conceived, capable of executing instructions stored in memory or storage or otherwise processing data. In a non-limiting example, the processor may include a microprocessor, field programmable gate array (FPGA), application-specific integrated circuit (ASIC), or other similar devices.

The memory may include various memories, as known in the art of the present disclosure or hereinafter conceived, including, but not limited to, L1, L2, or L3 cache or system memory. In a non-limiting example, the memory may include static random access memory (SRAM), dynamic RAM (DRAM), flash memory, read only memory (ROM), or other similar memory devices.

The user interface may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface.

The network interface may include one or more devices, as known in the art of the present disclosure or hereinafter conceived, for enabling communication with other hardware devices. In an non-limiting example, the network interface may include a network interface card (NIC) configured to communicate according to the Ethernet protocol. Additionally, the network interface may implement a TCP/IP stack for communication according to the TCP/IP protocols. Various alternative or additional hardware or configurations for the network interface will be apparent\

The storage may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage may store instructions for execution by the processor or data upon which the processor may operate. For example, the storage may store a base operating system for controlling various basic operations of the hardware. The storage may further store one or more application modules in the form of executable software/firmware.

More particularly, still referring to FIG. 3, robot pose controller 160 includes includes application module(s) (not shown) for rotating and translating surgical RCM robot 120 via platform 180 as known in the art of the present disclosure, for actuating revolute joints of surgical RCM robot 120 as previously described in the present disclosure for robot pose controller 60 (FIG. 1), and for tracking a pose of surgical RCM robot 120 within a robot coordinate system 121 as previously described in the present disclosure for robot pose controller 60 (FIG. 1).

Camera controller 161 includes application module(s) (not shown) for controlling a visualization by stereoscopic camera 140 and/or monocular camera of one or more landmark(s) of surgical RCM robot 120 on a temporal basis and generating landmark position data from the landmark visualization as previously described in the present disclosure for camera controllers 44 and 54 (FIG. 1).

Robot tracking controller 170 includes application module(s) in accordance with the inventive principles of the present disclosure for estimating a pose of surgical RCM robot 120 within a camera coordinate system as previously described in the present disclosure for robot tracking controller 70 (FIG. 1).

In one embodiment, robot tracking controller 170 embodies an arrangement of hardware, software, firmware and/or electronic circuitry structurally configuring translation vector estimator 171 for estimating a translation vector, a rotation matrix estimator 172 for estimating a rotation matrix and a robot pose estimator 173 for estimating the robot pose of surgical RCM robot 120 within the camera coordinate system based on the estimated translation vector and the rotation matrix.

Figure 4:
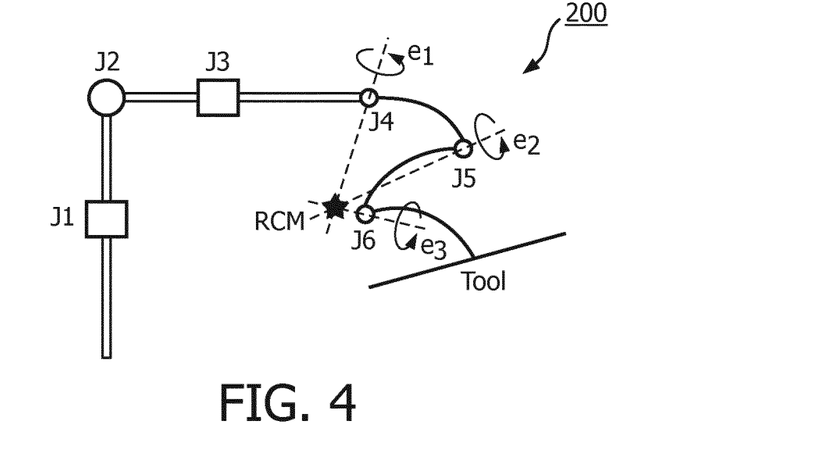
FIGS. 4-6 illustrates exemplary rotations of revolute joints of a RCM robot in accordance with the inventive principles of the present disclosure.
Figure 5:
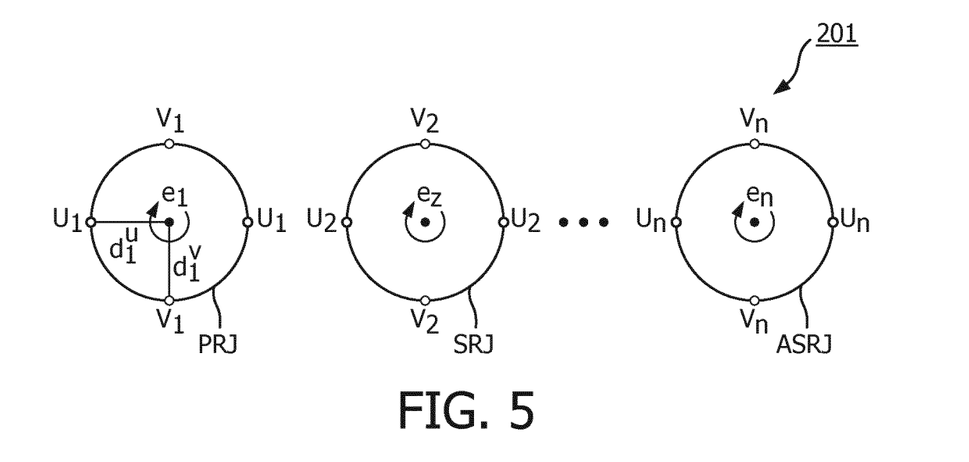

For purposes of describing exemplary embodiment of estimators 171-173, FIG. 4 illustrates a graphical model 200 of the joints of surgical RCM robot 120 and FIG. 5 illustrates a graphical model 201 of landmarks integrated into surgical RCM robot 120, both models being suitable for estimating a translation vector and a rotation matrix suitable for a stereoscopic visualization of landmarks integrated into surgical RCM robot 120 as previously describe in the present disclosure.

Referring to FIG. 4, graphical model 200 includes a joint J4 as a graphical representation of primary revolute joint and a joint J5 as a graphical representation of secondary revolute joint. A joint J6 is shown to highlight the applicability of the present disclosure to surgical RCM robot embodiments including additional secondary revolute joints.

Still referring to FIG. 4, graphical model includes a joint J1 for translation joint 182 of active arm 180 (FIG. 3), a joint J2 for rotational joint 183 of active arm 180 (FIG. 3) and a translation joint 184 of active arm 180 (FIG. 3).

Referring to FIG. 5, graphical model 211 includes a first unique landmark set of landmarks $u_1$ integrated onto a primary revolute joint PRJ and landmarks $u_2$ integrated onto a secondary revolute joint SRJ. Graphical model 211 includes a second unique landmark set of landmarks $v_1$ integrated onto a primary revolute joint PRJ and landmarks $v_2$ integrated onto a secondary revolute joint SRJ.

Referring to FIGS. 3-5, First, having set of $\pi$ unique landmarks $F = U \cup V = \{f_1, \ldots, f_n\}$ in the camera coordinate system (e.g., coordinate system 43 or coordinate system 53 as shown in FIG. 1), where landmark $f_i \in R^3$ ($f_i = \{x, y, z, 1\}^T$) is located at offset $d_i$ from the joint's i axis $e_i$, and $f_i \| e_i$ a motor axis in the camera coordinate system may be calculated in accordance with the following equations [1] and [2]:

$$e_i = \begin{bmatrix} I & R_i d \\ 0 & 1 \end{bmatrix}^{-1} f_i \qquad [1]$$

$$R_i = \begin{cases} (\hat{f}_i, 0) & \text{for } i = 1 \\ (\hat{f}_{i-1}, \theta_{i-1}) & \text{for } i > 1 \end{cases} \qquad [2]$$

where $R_i$ describes a rotation around axis defined by $f_i$ and angle $\theta_i$ of the joint i given by robot pose controller 160. Offset $d_i$ may be calculated either by (a) knowing the location of a single point on a motor axis $\hat{e}_i$ or (b) using a calibration method in which the offset is estimated at a known joints position (robot home position), such as, for example, as shown in FIG. 5.

Preferably, line feature vector $\hat{f}_i$ may be triangulated; having a set of corresponding 2D line segments detected on surgical RCM robot 120 from camera images as well as a calibrated system of stereo cameras, 3D feature vectors $\hat{f}_i \in R^3$ are triangulated using epipolar geometry i.e. 2D correspondence is transformed into 3D line by intersecting two planes passing through the respective camera centers, and 2D line segments. Alternatively, line feature vector $\hat{f}_i$ may be calculated by detected at least two points laying on the 2D line segments detected on the camera images.

Second, a translation vector t is found in a least square sense as a point that minimize the sum of squared distances between each motor axis $e_i$ and t in accordance with the following equations [3] and [4]:

$$t = \underset{t \in R^B}{\operatorname{argmin}} \sum_{i=1}^{n} \frac{|(e_i^2 - e_i^1) \times (e_i^1 - t)|^2}{|e_i^2 - e_i^1|^2} \qquad [3]$$

$$e_i = e_i^2 - e_i^1 \qquad [4]$$

Third, a rotation matrix R is defined by three vectors forming an orthonormal basis in accordance with the following equations [5]-[11]:

$$R = [\hat{x} \quad \hat{y} \quad \hat{z}] \qquad [5]$$

$$\hat{y} = \hat{e}_1 \qquad [6]$$

$$\hat{x} = \frac{\sum_{i=1}^{n} \left( \frac{n_i}{|n_i|} \right)}{n} \qquad [7]$$

$$n_i = \hat{y} \times (R_i \hat{e}_i) \qquad [8]$$

$$R_i = \begin{cases} (\hat{f}_i, 0) & \text{for } i = 1 \\ (\hat{f}_{i-1'} - \theta_{i-1}) & \text{for } i > 1 \end{cases} \qquad [9]$$

$$\hat{z} = \frac{z}{|z|} \qquad [10]$$

$$z = \hat{x} \times \hat{y} \qquad [11]$$

where $R_i$ describes a rotation around axis defined by $\hat{f}_i$ and angle $\theta_i$ of the joint given by robot pose controller 160.

Finally, the pose of the robot 120 in the camera coordinate system is defined in accordance with the following equation [12]:

$$T = [R \; t] \qquad [12]$$

Still referring to FIGS. 3-5, a second pose estimation embodiment, robot tracking controller 170 embodies a structural arrangement of hardware, software, firmware and/or electronic circuitry for a pose estimation involving an interpretation of landmark position data only to estimate a pose of surgical RCM robot 120 within a camera coordinate system (an "optical pose estimation").

This optical pose embodiment describes a special scenario in which the pose of robot 120 is calculated only using visual information (landmarks). Having a nonempty set $F = \{f_1, \ldots, f_n\}$ of non-parallel landmarks in $R^3$ that span the plane $P_F$ containing them, a pose of robot 120 may be calculated using following algorithm:

First, the intersection point w is found in a least square sense as a point that minimize the sum of squared distances between each axis defined by the landmarks $f_i$ and w in the following equations [13] and [14]:

$$w = \underset{w \in R^B}{\operatorname{argmin}} \sum_{i=1}^{n} \frac{|(f_i^2 - f_i^1) \times (f_i^1 - w)|^2}{|f_i^2 - f_i^1|^2} \quad [13]$$

$$f_i = f_i^2 - f_i^1 \quad [14]$$

Second, the translation vector t is found by offsetting the intersection point w by a scalar value $-d(x)_i$ in the direction defined by the normal $\hat{x}$ to the plane $P_F$ in accordance with the following equations {15]-[17]:

$$t = w - d(x)_i \cdot \hat{x} \quad [15]$$

$$\hat{x} = \frac{\sum_{i=1}^{n-1} \left(\frac{n_i}{|n_i|}\right)}{n-1} \quad [16]$$

$$n_i = \hat{f}_i \times \hat{f}_{i+1} \quad [17]$$

where the normal to the plane $\hat{x}$ is calculated per equation [16].

Third, the rotation matrix R is defined by three vectors forming an orthonormal basis in accordance with the following equations [18]-[21]:

$$R = [\hat{x} \ \hat{y} \ \hat{z}] \quad [18]$$

$$\hat{y} = \frac{f_1}{|f_1|} \quad [19]$$

$$\hat{z} = \frac{z}{|z|} \quad [20]$$

$$z = \hat{x} \times \hat{y} \quad [21]$$

Finally the pose of the robot 120 in the camera coordinate system is defined in accordance with the following equation [22]:

$$T = [R \ t] \quad [22]$$

Figure 6:
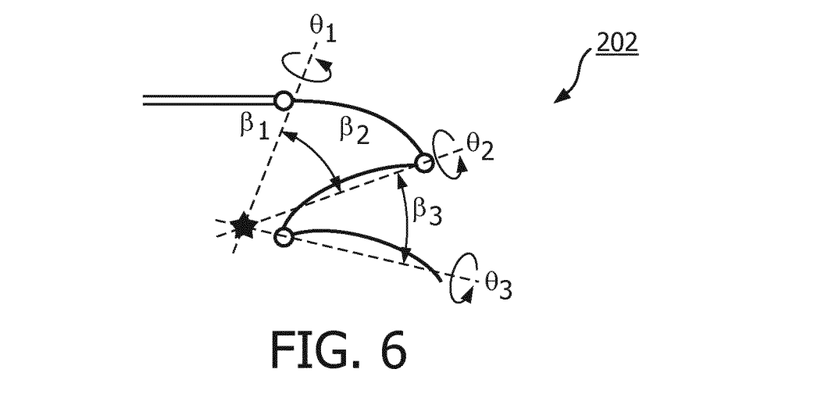

For purposes of describing another exemplary embodiment of estimators 171-173, FIG. 6 illustrates a graphical model 202 of the joints of surgical RCM robot 120 suitable for estimating a translation vector and a rotation matrix suitable for a monocular visualization of landmarks integrated into surgical RCM robot 120 as previously describe in the present disclosure.

Referring to FIG. 6, graphical model 202 includes a rotation angle $\Theta_1$ about a joint axis $\beta_1$ as a graphical representation of a primary revolute joint and a rotation angle $\Theta_2$ about a joint axis $\beta_2$ as a graphical representation of secondary revolute joint. A rotation angle $\Theta_3$ about a joint axis $\beta_3$ is shown to highlight the applicability of the present disclosure to surgical RCM robot embodiments including an additional secondary revolute joint.

Referring to FIGS. 3, 5 and 6, the camera/robot pose estimation describes a methodology for tracking and pose estimation of robot 120 using single calibrated optical camera which provides set $L=\{l_1, \ldots, l_n\}$ of unique 2D landmarks with a number of elements equal or larger than 3.

Having a set of landmarks $l_i \in R^2$ such as $l_i=[x, y, 1]^T$ in the image coordinate system, and a set of landmarks $r_i \in R^3$ such as $r_i[x, y, z, 1]^T$ in the robot coordinate system, a pose of the robot may be estimated by solving a PnP problem using methods know in art, such as RANSAC algorithm, based on the following equation [23]:

$$r_i = (KP)^{-1} l_i \quad [23]$$

where K is camera calibration matrix (intrinsic camera parameters), and P is a camera position and orientation in the world coordinate system (extrinsic camera parameters), which is calculated using the method described above (RANSAC algorithm).

Having set of landmark $l_i$ in the camera coordinate system, a set of landmarks $r_i$ is dynamically calculated in the robot coordinate system using following equation [24]:

$$r_i = \begin{bmatrix} I & R_i d \\ 0 & 1 \end{bmatrix} j_i \quad [24]$$

where d stands for an offset from the joint axis $j_i \in R^3$, such as $j_i=[x, y, z, 1]^T$, which is calculated per equation in accordance with the following equations [25] and [26] (and changed to homogenous representation):

$$j_i = \begin{bmatrix} r\cos(\frac{\pi}{2} - \beta_i) \\ r\sin(\frac{\pi}{2} - \beta_i) \end{bmatrix} \quad [25]$$

$$R_i = \begin{bmatrix} \cos(\beta_i) & 0 & \sin(\beta_i) \\ 0 & 1 & 0 \\ -\sin(\beta_i) & 0 & \cos(\beta_i) \end{bmatrix} \begin{bmatrix} \cos(\theta_i) & -\sin(\theta_i) & 0 \\ \sin(\theta_i) & \cos(\theta_i) & 0 \\ 0 & 0 & 1 \end{bmatrix} \quad [26]$$

where r stand for a radius of the concentric arches (distance between the RCM and the landmark), $\beta_i$ stands for the rotation angles between the joint rotation axis as shown in FIG. 6 and $\theta_i$ stands for the rotation angle around the joint rotation axis as shown in FIG. 6.

Referring back to FIG. 3, robot pose controller 160, camera controller 161 and/or robot tracking controller 170 may be alternatively or concurrently installed on other types of processing devices including, but not limited to, a tablet or a server accessible by workstations and tablets, or may be distributed across a network supporting an execution of pose estimation of the present disclosure.

Also in practice, robot pose controller 160, camera controller 161 and/or robot tracking controller 170 may be integrated components, segregated components or logically partitioned components of markerless robot tracking device 111.

Also in practice, camera controller may be omitted from device 111 and installed on a separate optical position measurement system.

Referring to FIGS. 1-4, those having ordinary skill in the art will appreciate numerous benefits of the present disclosure including, but not limited to, an improvement over marker based tracking systems, controllers and methods by the inventions of the present disclosure providing an integration of trackable landmarks into a surgical RCM robot that may be utilized in any type of image-guided intervention (e.g., minimally invasive laparoscopic surgery and minimally invasive surgery the spine).

Furthermore, as one having ordinary skill in the art will appreciate in view of the teachings provided herein, features, elements, components, etc. described in the present disclosure/specification and/or depicted in the Figures may be implemented in various combinations of electronic components/circuitry, hardware, executable software and executable firmware and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present disclosure can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk-read only memory (CD-ROM), compact disk-read/write (CD-R/W) and DVD. Further, it should be understood that any new computer-readable medium which may hereafter be developed should also be considered as computer-readable medium as may be used or referred to in accordance with exemplary embodiments of the present disclosure and disclosure.

Having described preferred and exemplary embodiments of novel and inventive markerless robot tracking systems, controllers and methods, (which embodiments are intended to be illustrative and not limiting), it is noted that modifications and variations can be made by persons having ordinary skill in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A markerless robot tracking system, comprising:
a surgical remote center of motion (RCM) robot transitionable between a plurality of robot poses within a robot coordinate system,
wherein the surgical RCM robot includes a primary revolute joint rotatable about a primary rotational axis, and
wherein the surgical RCM robot further includes a secondary revolute joint rotatable about a secondary rotational axis;
a plurality of unique landmark sets,
wherein each unique landmark set includes at least one landmark integrated into the surgical RCM robot at a fixed orientation relative to the primary rotational axis, and
wherein each unique landmark set further includes an additional at least one landmark integrated into the surgical RCM robot at a fixed orientation relative to the secondary rotational axis;
an optical camera structurally configured to visualize at least a subset of the plurality of unique landmark sets within a camera coordinate system; and
a robot tracking controller structurally configured to control an estimation of a robot pose of the surgical RCM robot within the camera coordinate system in response to receiving a visualization by the optical camera of the at least the subset of the plurality of unique landmark sets within the camera coordinate system.

2. The markerless robot tracking system of claim 1, further comprising:
a camera controller structurally configured to control the visualization by the optical camera of the at least the subset of the plurality of unique landmark sets within the camera coordinate system,
wherein the camera controller is further structurally configured to generate landmark position data informative of a positioning of the primary revolute joint and of the secondary revolute joint within the camera coordinate system derived from the visualization by the optical camera of the at least the subset of the plurality of unique landmark sets within the camera coordinate system;
wherein, in response to receiving a generation of the landmark position data by the camera controller, the robot tracking controller is further structurally configured to estimate a translation alignment between the robot coordinate system and the camera coordinate system; and wherein the robot tracking controller is further structurally configured to estimate the robot pose of the surgical RCM robot within the camera coordinate system based on the translation alignment.

3. The markerless robot tracking system of claim 1, a camera controller structurally configured to control the visualization by the optical camera of the at least the subset of the plurality of unique landmark sets within the camera coordinate system, wherein the camera controller is further structurally configured to generate landmark position data informative of a positioning of the primary revolute joint and of the secondary revolute joint within the camera coordinate system derived from the visualization by the optical camera of the at least the subset of the plurality of unique landmark sets within the camera coordinate system;

wherein, in response to receiving a generation of the landmark position data by the camera controller, the robot tracking controller is further structurally configured to estimate a rotational orientation between the robot coordinate system and the camera coordinate system; and wherein the robot tracking controller is further structurally configured to estimate the robot pose of the surgical RCM robot within the camera coordinate system based on the rotation orientation.

4. The markerless robot tracking system of claim 3, wherein, in response to receiving a generation of the landmark position data by the camera controller, the robot tracking controller is further structurally configured to estimate a translation alignment between the robot coordinate system and the camera coordinate system; and wherein the robot tracking controller is further structurally configured to estimate the robot pose of the surgical RCM robot within the camera coordinate system based on the translation alignment and the rotation orientation.

5. The markerless robot tracking system of claim 2, further comprising:

a robot pose controller structurally configured to control a transition of the surgical RCM robot between the plurality of robot poses within a robot coordinate system, wherein the robot pose controller is structurally configured to generate revolute joint position data informative of a rotational position of the primary revolute joint relative to the primary rotational axis and of rotational position of the secondary revolute joint relative to the secondary rotational axis;

wherein, in response to receiving a generation of the landmark position data by the camera controller and a generation of the revolute joint position data by the robot pose controller, the robot tracking controller is further structurally configured to estimate a translation alignment between the robot coordinate system and the camera coordinate system; and wherein the robot tracking controller is further structurally configured to estimate the robot pose of the surgical RCM robot within the camera coordinate system based on the translation alignment.

6. The markerless robot tracking system of claim 3, a robot pose controller structurally configured to control a transition of the surgical RCM robot between the plurality of robot poses within a robot coordinate system, wherein the robot pose controller is structurally configured to generate revolute joint position data informative of a rotational position of the primary revolute joint relative to the primary rotational axis and of rotational position of the secondary revolute joint relative to the secondary rotational axis;

wherein, in response to receiving a generation of the landmark position data by the camera controller and a generation of the revolute joint position data by the robot pose controller, the robot tracking controller is further structurally configured to estimate a rotational orientation between the robot coordinate system and the camera coordinate system; and wherein the robot tracking controller is further structurally configured to estimate the robot pose of the surgical RCM robot within the camera coordinate system based on the rotational orientation.

7. The markerless robot tracking system of claim 6, wherein, in response to receiving a generation of the landmark position data by the camera controller and a generation of the revolute joint position data by the robot pose controller, the robot tracking controller is further structurally configured to estimate a translation alignment between the robot coordinate system and the camera coordinate system; and wherein the robot tracking controller is further structurally configured to estimate the robot pose of the surgical RCM robot within the camera coordinate system based on the translation alignment and the rotation orientation.

8. A markerless robot tracking device for a surgical remote center of motion (RCM) robot transitionable between a plurality of robot poses within a robot coordinate system, the surgical RCM robot including a primary revolute joint rotatable about a primary rotational axis and a secondary revolute joint rotatable about a secondary rotational axis, a plurality of unique landmark sets being integrated into surgical RCM robot, wherein each unique landmark set includes at least one landmark integrated into the surgical RCM robot at a fixed orientation relative to the primary rotational axis, and wherein each unique landmark set further includes an additional at least one landmark integrated into the surgical RCM robot at a fixed orientation relative to the secondary rotational axis, the markerless robot tracking device comprising:

a robot tracking controller, wherein the robot tracking controller is structurally configured to control an estimation of a robot pose of the surgical RCM robot within a camera coordinate system in response to receiving a visualization by an optical camera of the at least the subset of the plurality of unique landmark sets within the camera coordinate system, and wherein the robot tracking controller is further structurally configured to generate surgical RCM robot pose data informative of the estimation of the robot pose of the surgical RCM robot within the camera coordinate system.

9. The markerless robot tracking device of claim 8,
wherein the robot tracking controller is operable to receive landmark position data informative of a positioning of the primary revolute joint and of the secondary revolute joint within the camera coordinate system derived from the visualization by the optical camera of the at least the subset of the plurality of unique landmark sets within the camera coordinate system;
wherein the robot tracking controller includes
at least one of a translation alignment estimator structurally configured to estimate a translation alignment between the robot coordinate system and the camera coordinate system in response to receiving the landmark position data, and a rotational orientation estimator structurally configured to estimate a rotational orientation between the robot coordinate system and the camera coordinate system in response to receiving the landmark position data; and
a pose estimator structurally configured to estimate the robot pose of the surgical RCM robot within the camera coordinate system based on at least one of the translation alignment and the rotational orientation.

10. The markerless robot tracking device of claim 8, further comprising:
a camera controller structurally configured to control the visualization by the optical camera of the at least the subset of the plurality of unique landmark sets within the camera coordinate system,
wherein the camera controller is further structurally configured to generate landmark position data informative of a positioning of the primary revolute joint and of the secondary revolute joint within the camera coordinate system derived from the visualization by the optical camera of the at least the subset of the plurality of unique landmark sets within the camera coordinate system;
wherein, in response to receiving a generation of the landmark position data by the camera controller, the robot tracking controller is further structurally configured to estimate a translation alignment between the robot coordinate system and the camera coordinate system; and
wherein the robot tracking controller is further structurally configured to estimate the robot pose of the surgical RCM robot within the camera coordinate system based on the translation alignment.

11. The markerless robot tracking device of claim 8,
a camera controller structurally configured to control the visualization by the optical camera of the at least the subset of the plurality of unique landmark sets within the camera coordinate system,
wherein the camera controller is further structurally configured to generate landmark position data informative of a positioning of the primary revolute joint and of the secondary revolute joint within the camera coordinate system derived from the visualization by the optical camera of the at least the subset of the plurality of unique landmark sets within the camera coordinate system;
wherein, in response to receiving a generation of the landmark position data by the camera controller, the robot tracking controller is further structurally configured to estimate a rotational orientation between the robot coordinate system and the camera coordinate system; and
wherein the robot tracking controller is further structurally configured to estimate the robot pose of the surgical RCM robot within the camera coordinate system based on the rotation orientation.

12. The markerless robot tracking device of claim 11,
wherein, in response to receiving a generation of the landmark position data by the camera controller, the robot tracking controller is further structurally configured to estimate a translation alignment between the robot coordinate system and the camera coordinate system; and
wherein the robot tracking controller is further structurally configured to estimate the robot pose of the surgical RCM robot within the camera coordinate system based on the translation alignment and the rotation orientation.

13. The markerless robot tracking device of claim 10, further comprising:
a robot pose controller structurally configured to control a transition of the surgical RCM robot between the plurality of robot poses within a robot coordinate system,
wherein the robot pose controller is structurally configured to generate revolute joint position data informative of a rotational position of the primary revolute joint relative to the primary rotational axis and of rotational position of the secondary revolute joint relative to the secondary rotational axis;
wherein, in response to receiving a generation of the landmark position data by the camera controller and a generation of the revolute joint position data by the robot pose controller, the robot tracking controller is further structurally configured to estimate a translation alignment between the robot coordinate system and the camera coordinate system; and
wherein the robot tracking controller is further structurally configured to estimate the robot pose of the surgical RCM robot within the camera coordinate system based on the translation alignment.

14. The markerless robot tracking device of claim 10,
a robot pose controller structurally configured to control a transition of the surgical RCM robot between the plurality of robot poses within a robot coordinate system,
wherein the robot pose controller is structurally configured to generate revolute joint position data informative of a rotational position of the primary revolute joint relative to the primary rotational axis and of rotational position of the secondary revolute joint relative to the secondary rotational axis;
wherein, in response to receiving a generation of the landmark position data by the camera controller and a generation of the revolute joint position data by the robot pose controller, the robot tracking controller is further structurally configured to estimate a rotational orientation between the robot coordinate system and the camera coordinate system; and
wherein the robot tracking controller is further structurally configured to estimate the robot pose of the surgical RCM robot within the camera coordinate system based on the rotational orientation.

15. The markerless robot tracking device of claim 14,
wherein, in response to receiving a generation of the landmark position data by the camera controller and a generation of the revolute joint position data by the robot pose controller, the robot tracking controller is further structurally configured to estimate a translation alignment between the robot coordinate system and the camera coordinate system; and wherein the robot tracking controller is further structurally configured to estimate the robot pose of the surgical RCM robot within the camera coordinate system based on the translation alignment and the rotation orientation.

16. A markerless robot tracking method comprising:

a surgical RCM robot selectively transitioned between a plurality of robot poses within a robot coordinate system,
  wherein the surgical RCM robot includes a primary revolute joint rotatable about a primary rotational axis and a secondary revolute joint rotatable about a secondary rotational axis,
  wherein a plurality of unique landmark sets are integrated into surgical RCM robot,
  wherein each unique landmark set includes at least one landmark integrated into the surgical RCM robot at a fixed orientation relative to the primary rotational axis, and
  wherein each unique landmark set further includes an additional at least one landmark integrated into the surgical RCM robot at a fixed orientation relative to the secondary rotational axis;

an optical camera visualizing at least a subset of the plurality of unique landmark sets within a camera coordinate system; and a robot tracking controller controlling an estimation of a robot pose of the surgical RCM robot within the camera coordinate system derived from the visualizing by the optical camera of the least the subset of the plurality of unique landmark sets within the camera coordinate system.

17. The markerless robot tracking method of claim 16, further comprising:

a camera controller controlling the visualization by the optical camera of the at least the subset of the plurality of unique landmark sets within the camera coordinate system,
  wherein the camera controller generates landmark position data informative of a positioning of the primary revolute joint and of the secondary revolute joint within the camera coordinate system derived from the visualization by the optical camera of the at least the subset of the plurality of unique landmark sets within the camera coordinate system; and the robot tracking controller estimating a translation alignment between the robot coordinate system and the camera coordinate system in response to the generation of the landmark position data by the camera controller,
  wherein the robot tracking controller is further structurally configured to estimate the robot pose of the surgical RCM robot within the camera coordinate system based on the translation alignment.

18. The markerless robot tracking method of claim 17, further comprising:

a robot pose controller controlling a transition of the surgical RCM robot between the plurality of robot poses within a robot coordinate system,
  wherein the robot pose controller generate revolute joint position data informative of a rotational position of the primary revolute joint relative to the primary rotational axis and of rotational position of the secondary revolute joint relative to the secondary rotational axis; and the robot tracking controller estimating a translation alignment between the robot coordinate system and the camera coordinate system in response to a generation of the landmark position data by the camera controller and a generation of the revolute joint position data by the robot pose controller,
  wherein the robot tracking controller estimates the robot pose of the surgical RCM robot within the camera coordinate system based on the translation alignment.

19. The markerless robot tracking method of claim 16, further comprising:

a camera controller controlling the visualization by the optical camera of the at least the subset of the plurality of unique landmark sets within the camera coordinate system,
  wherein the camera controller generates landmark position data informative of a positioning of the primary revolute joint and of the secondary revolute joint within the camera coordinate system derived from the visualization by the optical camera of the at least the subset of the plurality of unique landmark sets within the camera coordinate system; and the robot tracking controller estimating a rotational orientation between the robot coordinate system and the camera coordinate system in response to the generation of the landmark position data by the camera controller,
  wherein the robot tracking controller is further structurally configured to estimate the robot pose of the surgical RCM robot within the camera coordinate system based on the rotational orientation.

20. The markerless robot tracking method of claim 19, further comprising:

a robot pose controller controlling a transition of the surgical RCM robot between the plurality of robot poses within a robot coordinate system,
  wherein the robot pose controller generate revolute joint position data informative of a rotational position of the primary revolute joint relative to the primary rotational axis and of rotational position of the secondary revolute joint relative to the secondary rotational axis; and the robot tracking controller estimating a rotational orientation between the robot coordinate system and the camera coordinate system in response to a generation of the landmark position data by the camera controller and a generation of the revolute joint position data by the robot pose controller,
  wherein the robot tracking controller estimates the robot pose of the surgical RCM robot within the camera coordinate system based on the rotational orientation.

* * * * *